United States Patent [19]

Pellico

[11] Patent Number: 5,336,494
[45] Date of Patent: Aug. 9, 1994

[54] PET CHEWABLE PRODUCTS WITH ENZYMATIC COATING

[76] Inventor: Michael A. Pellico, 3024 Military Ave., Los Angeles, Calif. 90272

[21] Appl. No.: 10,841

[22] Filed: Jan. 29, 1993

[51] Int. Cl.$^5$ ............................................. A61K 37/50
[52] U.S. Cl. .................... 424/94.4; 424/94.1; 424/94.2; 424/94.61; 424/441; 424/94.3
[58] Field of Search .................. 424/442, 441, 94.4, 424/94.1, 94.2, 94.61, 94.3

[56] References Cited

U.S. PATENT DOCUMENTS

| | | | |
|---|---|---|---|
| 4,150,113 | 4/1979 | Hoogendoorn | 424/50 |
| 4,178,362 | 12/1979 | Hoogendoorn | 424/48 |
| 4,269,822 | 5/1981 | Pellico | 424/50 |
| 4,537,764 | 8/1985 | Pellico | 424/50 |
| 4,569,519 | 1/1986 | Pellico | 424/48 |
| 4,576,817 | 3/1986 | Montgomery | 424/94 |
| 4,578,265 | 3/1986 | Pellico | 424/50 |
| 4,617,190 | 10/1986 | Montgomery | 426/50 |
| 5,114,704 | 5/1992 | Spanier | 424/57 |

*Primary Examiner*—Gabrielle Phelan
*Attorney, Agent, or Firm*—Donald Diamond

[57] ABSTRACT

An orally chewable, enzymatically coated product is provided which, upon chewing, produces an anti-bacterial and bacteriostatic effect in the oral cavity by activation of an enzymatic system contained within the coating. The enzymatic surface coating is developed, in substantially dry form, from a thickened, aqueous coating solution having a viscosity from about 1,000 to about 50,000 centipoises and containing oxidizable substrate and oxidoreductase enzymes specific to such substrate for producing hydrogen peroxide upon oral chewing of the coated product and optionally, but advantageously, further containing peroxidatic peroxidase and an alkali metal salt of an oxygen accepting anion for interacting with hydrogen peroxide to produce oxidized anionic bacterial inhibitor. An illustrative enzymatic system for this purpose contains glucose, glucose oxidase, potassium thiocyanate and lactoperoxidase. The thickened enzymatic solution suppresses the enzymatic reaction during the preparation and application of the solution to the surface of the chewable product.

18 Claims, No Drawings

PET CHEWABLE PRODUCTS WITH ENZYMATIC COATING

BACKGROUND OF THE INVENTION

1. Field of the Invention

This invention relates to oral care products and, more particularly, to orally chewable, enzymatically coated products which, upon chewing, produce an anti-bacterial and bacteriostatic effect in the oral cavity by activation of an enzymatic system contained within the coating. 2. Prior Art It is disclosed in the prior art that enzymatic anti-bacterial systems can be incorporated into oral care products and other products such as powder milk (U.S. Pat. No. 4,617,190)and bandages (U.S. Pat. No. 4,576,817) for producing an anti-bacterial effect in a defined environment.

U.S. Pat. No. 4,150,113 (Hoogendoorn et al., 1979) and U.S. Pat. No. 4,178,362 (Hoogendoorn et al., 1979) disclose, respectively, an enzymatic toothpaste and an enzymatic chewable dentifrice containing glucose oxidase which acts on glucose present in saliva and tooth plaque to produce hydrogen peroxide. The patentees note that oral bacterial, through enzyme systems having SH-GROUPS, effect glycolysis of food products containing sugars and point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

U.S. Pat. No. 4,537,764 (Pellico et al., 1985) discloses an enzymatic dentifrice containing Beta-D-Glucose and glucose oxidase for producing hydrogen peroxide upon oral application of the dentifrice, with pre-application stability being maintained by limiting any water in the dentifrice to not more than about 10 wt. % based on the weight of the dentifrice.

U.S. Pat. No. 4,578,365 (Pellico et al., 1986) discloses a di-enzymatic dentifrice which contains, for example, glucose and glucose oxidase for producing hydrogen peroxide upon oral application of the dentifrice and further contains a thiocyanate salt and lactoperoxidase for interacting with hydrogen peroxide to produce a hypothiocyanate ( sic ) with pre-application stability being maintained by limiting any water in the dentifrice to not more than about 10 wt. % based on the weight of the dentifrice.

U.S. Pat. No. 4,564,519 (Pellico et al., 1986)discloses a di-enzymatic chewable dentifrice which contains, for example, glucose and glucose oxidase for producing hydrogen peroxide upon chewing the dentifrice and further contains a thiocyanate salt and lactoperoxidase for interacting with hydrogen peroxide to produce a hypothiocyanate (sic) bacterial inhibitor, with pre-application stability being maintained by limiting any unbound water in the chewable dentifrice to an amount not more than about 1.0 wt. % and limiting the total water, bound and unbound, to not more than about 10 wt. %.

The use of enzymatic anti-bacterial toothpaste having an enzyme system as described in U.S. Pat. No. 4,537,764 and U.S. Pat. No. 4,578,265 has been expanded to include oral pet care, with emphasis being placed on the use of such toothpaste in the brushing of the teeth of dogs and cats. While this application of enzymatic toothpaste constitutes an improvement in pet care, it has been noted in some cases, that pet owners do not brush their dogs' teeth on a daily basis for a prescribed length of time and, in other cases, it has been noted that some dogs, particularly older dogs, resist the brushing of their teeth. Accordingly, it would be advantageous to provide an anti-bacterial enzymatic deliver system for oral pet care that does not depend upon dental brushing and which is readily accepted as an oral product by the pet.

It is known in the art to convert rawhide, beef hide and the like into various configurations and shapes for use as chewable products by pets, particularly, dogs. It is also known in the art to provide chewable products for pets with coatings which incorporate flavor compositions. The addition of orally actuated, anti-bacterial enzymatic systems to pet chewable products such as rawhide and beef hide would be highly beneficial in that enhanced oral care would be achieved in a simplistic manner with pet receptive products.

SUMMARY OF THE INVENTION

In accordance with one aspect of this invention, there is provided an orally chewable, enzymatically coated product wherein the enzymatic coating is developed, in substantially dry form, from an enzymatic solution comprising a fluidic component and an enzymatic component, wherein:

(a) the fluidic component contains water and non-toxic water soluble thickener in an amount to provide the enzymatic solution with a viscosity from about 1,000 to about 50,000 centipoises; and (b) the enzymatic component comprises an enzymatic system containing, per gram of fluidic component, from about 0.015 to about 0.6 millimole of oxidizable substrate and from about 0.5 to about 5,000 International Units of oxidoreductase enzyme specific to such substrate for producing hydrogen peroxide upon oral chewing of the enzymatically coated product.

In accordance with a second aspect of this invention, there is provided a method for preparing an orally chewable, enzymatically coated product which comprises:

(a) applying an enzymatic solution comprising a fluidic component and an enzymatic component to a chewable product, wherein:

(1) the fluidic component contains water and non-toxic water soluble thickener in an amount to provide the enzymatic solution with a viscosity from about 1,000 to about 50,000 centipoises; and (2) the enzymatic component comprises an enzymatic system containing, per gram of fluidic component, from about 0.015 to about 0.6 millimole of oxidizable substrate and from about 0.5 to about 5,000 International Units of oxidoreductase enzyme specific to such substrate for producing hydrogen peroxide upon oral chewing of the enzymatically coated product; and (b) thereafter drying the coated product.

In accordance with a third aspect of this invention, the enzymatic system of the enzymatic component, as above described with respect to the first and second aspects of this invention, further contains, per gram of fluidic component, from about 0.1 to about 10,000 International Units of peroxidatic peroxidase and from about 0.001 to about 0.01 millimole of an alkali metal salt of an oxygen accepting anion selected from the group consisting of thiocyanate, chloride and iodide or a mixture of such salts for interacting with hydrogen peroxide to produce an oxidized anionic bacterial inhibitor.

DETAILED DESCRIPTION

The enzymatic, pet chewable products of this invention comprise a non-toxic, pet chewable base that incorporates an enzymatic coating for producing an anti-bacterial and a bacteriostatic effect upon oral chewing of the enzymatic product.

Chewable bases which can be used in the practice of this invention include rawhide, beef hide, non-toxic plastics and similar products. The chewable base can be in any suitable form such as thin strips or enlarged forms of varying configurations.

The enzymatic coating is developed on the chewable base, in substantially dry form, from an enzymatic solution comprising a fluidic component and an enzymatic component.

The fluidic component contains water and non-toxic, water soluble thickener, with the amount of the thickener being selected so as to provide the fluidic component with a viscosity generally from about 1,000 to about 50,000 centipoises, with an intermediate viscosity being from about 5,000 to about 50,000 centipoises and a preferred viscosity being from about 10,000 to about 50,000 centipoises. Viscosity determinations can be made by utilizing a suitable viscometer in accordance with applicable procedures well known in the art.

Thickeners which can be advantageously used in the practice of this invention to provide the requisite viscosity include gelatin, carboxymethylcellulose, agar-agar, high viscosity starch, polyvinyl alcohol, carrageen and thickener equivalents thereof.

The enzymatic component comprises a first enzyme system containing an oxidizable substrate and an oxidoreductase enzyme specific to such substrate for producing hydrogen peroxide upon oral chewing of the enzymatically coated chewable product, with the chemical environment of the oral cavity providing the source of additional reactant (oxygen) or reactants (oxygen, water) to effect the enzymatic reaction. Illustrative examples of oxidoreductase enzymes and their corresponding oxidizable substrates which can be used in the practice of this invention are set forth in the following table:

TABLE A

| OXIDOREDUCTASE ENZYME | OXIDIZABLE SUBSTRATE |
|---|---|
| Glucose Oxidase | B-D-glucose |
| Hexose Oxidase | Hexose |
| Galactose Oxidase | D-galactose |
| Pyranose Oxidase | Pyranose |
| Pyruvate Oxidase | Pyruvate |
| Oxalate Oxidase | Oxalate |
| DL-Aminoacid Oxidase | DL-Aminoacid |

In an illustrative reaction, glucose oxidase catalyzes the interaction of Beta-D-glucose, water and oxygen during the oral chewing of the enzymatically coated product to produce hydrogen peroxide and gluconic acid.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

The oxidizable substrate is generally present in the fluidic component in an amount from about 0.015 to about 0.6 millimole per gram of fluidic component and, preferably, from about 0.025 to about 0.1 millimole per gram of fluidic component while the oxidoreductase enzyme specific to the substrate is generally present in the fluidic component in an amount from about 0.5 to about 5,000 International Units (hereinafter sometimes abbreviated IU) per gram of fluidic component and, preferably, from about 10 to about 1,000 IU per gram of fluidic component. The term millimole identifies that quantity in grams corresponding to the molecular weight of the composition divided by one thousand. The term International Unit(s) identifies that amount of enzyme that will effect catalysis of 1.0 micromole of substrate per unit at pH 7.0 and 25° C. Oxidoreductase enzymes are supplied in dry or liquid form with the label specifying the concentration in International Units on a per gram or per milliliter basis, as appropriate.

In addition to the first enzyme system comprising oxidizable substrate and oxidoreductase enzyme specific to such substrate for producing hydrogen peroxide, the fluidic component of this invention is advantageously provided with a second enzyme system containing a peroxidatic peroxidase and an alkali metal salt of an oxygen accepting anion for interacting with hydrogen peroxide to produce an oxidized anionic bacterial inhibitor.

Peroxidases which can be used in the practice of this invention include lactoperoxidase, horse radish peroxidase, iodide peroxidase, chloride peroxidase and myeloperoxidase. Oxidizable salts which can be used in the practice of this invention include, for example, the thiocyanate, chloride or iodide salt of sodium, potassium, ammonium, calcium or magnesium or mixtures of such salts. In the presence of hydrogen peroxide, the oxygen accepting anions of the aforesaid salts, namely, thiocyanate, chloride and iodides are oxidized to hypothiocyanite, hypochlorite and hypoiodite, respectively.

The peroxidase is generally present in the fluidic component in an amount from about 0.1 to about 10,000 International Units per gram of fluidic component and, preferably, from about 10 to about 1,500 International Units per gram of fluidic component while the oxidizable salt is generally present in the fluidic component in an amount from about 0.0001 to about 0.01 millimole per gram of fluidic component and, preferably, from about 0.001 to about 0.006 millimole per gram of fluidic component.

The operable integrity of the enzymatic system can be affected by catalase which is present in commercial glucose oxidase as well as mucous membrane tissue. Catalase, which is extraneous to the enzymatic system of this invention, competes with peroxidaticperoxidase for hydrogen peroxide. In order to reduce loss of hydrogen peroxide through the presence of catalase, an effective amount of an enzymatic inhibitor specific to catalase can be advantageously incorporated into the enzymatic solution. An ascorbic salt such as sodium ascorbate, potassium ascorbate, ascorbyl palmitate, or mixtures thereof can be used as an enzymatic inhibitor which is specific to catalase. An effective amount of ascorbate salt for catalase inhibition is from about 0.000001 to about 0.0001 millimole per gram of fluidic component. Iron salts such as ferrous sulphate can be incorporated into the enzymatic solution as a potentiator for ascorbate salt in its role as catalase inhibitor.

The enzymatic solution of this invention may advantageously be formulated with an aminohexose as, for example, an aminoglucose such as glucosamine, N-actyl glucosamine or mixtures thereof in order to increase the yield or accumulation of oxidized anionic bacterial inhibitor. The aminoglucose is generally present in the enzymatic solution in an amount from about 0.0001 to about 0.002 millimole per gram of fluidic component and, preferably, in an amount from about 0.003 to about 0.001 millimole per gram of fluidic component.

The enzymes described herein may be advantageously encapsulated to enhance storage ability in the enzymatic-coating. The encapsulating material can be composed of a water soluble polymer or a polymer permeable to a substrate specific to the enzyme or enzymes contained therein. An illustrative encapsulating material is carboxymethylcellulose.

In addition to the thickener and the enzymatic system, the enzymatic solution can be formulated with a plasticizer such as glycerine and propylene glycol, with an abrasive such as aluminum oxide and with a non-stick coating material such as mineral oil.

The enzymatically coated, pet chewable products are prepared by brushing or spraying the chewable product with the enzymatic solution or by dipping the chewable product into the enzymatic solution and thereafter air drying the coated product.

For spray application, the viscosity of the enzymatic solution should not exceed about 20,000 centipoises; for dipping application, the viscosity of the enzymatic solution should not exceed about 25,000 centipoises; and for brush application, the viscosity of the enzymatic solution should not exceed about 50,000 centipoises.

The thickened enzymatic solution can be prepared from heat soluble thickeners such as gelatin, high viscosity starch and agar-agar, as well as from ambient soluble thickeners such as carboxymethylcellulose. When a heat soluble thickener is used as the thickening agent, the aqueous admixture thereof together with non-heat-sensitive ingredients of the formulation are heated, with stirring, to about 100° C. to solubilize the thickener and thereafter the solution is cooled to about 55° C. to permit the addition, with continued stirring, of heat sensitive ingredients which include the heat sensitive enzymes. The relatively hot enzymatic solution is applied to the pet chewable base in accordance with one of the application methods hereinabove described and the liquid, enzymatic coating is then dried to form a yieldable hard coating. When an ambient soluble thickener is used as the thickening agent, the thickener and other ingredients are added to water, with stirring, to form the thickened enzymatic solution, with the proviso that the shear sensitive ingredients, which include the enzymes, are added last to minimize shear impact on the enzymes.

In U.S. Pat. No. 4,578,265 (Pellico et al., 1986) which relates to enzymatic dentifrice compositions, it is disclosed that since water promotus the oxidation/reduction reaction of an enzyme system containing an oxidizable substrate and an oxidoreductase enzyme specific to such substrate for producing hydrogen peroxide and is also a reactant in certain of these enzymatic reactions, it has been found to be essential to limit any water present in the dentifrice to an amount not more than about 10 wt. % so as to impart maximum stability and shelf life to the compositions.

U.S. Pat. No. 4,564,519 (Pellico et al., 1986), which relates to the use of an oxidoreductase enzyme system in chewing gum, discloses that it has been found to be essential to limit any unbound water present in the chewing gum to an amount not more than about 1.0 wt. % and to limit the total water, bound and unbound, to not more than about 10 wt. %.

In contrast to the aforesaid prior art, and in accordance with this invention, it has now been found that oxidoreductase enzyme stability can be maintained in an aqueous environment that contains well in excess of 10 wt. % water, as shown by the examples hereinafter set forth, when a thickener is used in the aqueous formulation so as to provide a viscosity of at least about 1,000 centipoises.

EXAMPLE 1

This example illustrates an enzymatic coating solution containing gelatin and glucose oxidase.

| Composition | Weight, grams |
| --- | --- |
| Gelatin | 15 |
| Glycerine | 44 |
| Water | 30 |
| Mineral oil | 5 |
| Glucose oxidase (600 IU) | 0.006 |

The enzymatic solution is prepared by adding gelatin, glycerine and mineral oil to the water and heating the admixture to 212° F., to form a solution, and thereafter cooling the solution 125° F. and adding, with stirring, the glucose oxidase to obtain the enzymatic coating composition.

EXAMPLE 2

This example illustrates an enzymatic coating solution containing gelatin and glucose oxidase together with glucose.

| Composition | Weight, grams |
| --- | --- |
| Gelatin | 15 |
| Glycerine | 44 |
| Water | 35 |
| Glucose | 6 |
| Glucose oxidase (300 IU) | 0.003 |

The enzymatic solution was prepared by adding gelatin, glycerine and glucose to the water and heating the admixture to 212° F. to form a solution, and thereafter cooling the solution to 125° F. and adding, with stirring, the glucose oxidase to obtain the enzymatic coating composition. The viscosity of the solution was greater than 16,000 centipoises.

EXAMPLE 3

This example illustrates an enzymatic coating solution containing carboxymethylcellulose and glucose oxidase together with glucose.

| Composition | Weight, grams |
| --- | --- |
| Carboxymethylcellulose | 6 |
| Glycerine | 53 |
| Water | 35 |

-continued

| Composition | Weight, grams |
| --- | --- |
| Glucose | 6 |
| Glucose oxidase (300 IU) | 0.003 |

The enzymatic solution was prepared by adding carboxymethylcellulose at ambient temperature, and with constant stirring, to glycerine, glucose and water to form a solution, and thereafter adding glucose oxidase, with continued stirring, to obtain the enzymatic coating composition. The viscosity of the solution was 8,000 centipoises.

EXAMPLE 4

This example illustrates an enzymatic coating solution containing agar-agar together with glucose, glucose oxidase and lactoperoxidase.

| Composition | Weight, grams |
| --- | --- |
| Agar-agar | 10 |
| Glycerine | 15 |
| Water | 65 |
| Glucose | 10 |
| Glucose oxidase (500 IU) | 0.005 |
| Lactoperoxidase (200 IU) | 0.002 |

The enzymatic solution was prepared by adding the agar-agar, glycerine and glucose to water and heating the admixture to 212° F. to form a solution, and thereafter cooling the solution 120° F. and adding, with stirring the glucose coating composition. The viscosity of the solution was 12,000 centipoises.

EXAMPLE 5

This example illustrates an enzymatic coating solution containing high viscosity starch together with glucose, glucose oxidase, myeloperoxidase and potassium thiocyanate.

| Composition | Weight, grams |
| --- | --- |
| High viscosity starch | 20 |
| Sorbitol | 25 |
| Water | 40 |
| Glycerine | 5 |
| Glucose | 10 |
| Glucose oxidase (500 IU) | 0.005 |
| Myeloperoxidase (100 IU) | 0.001 |
| Potassium thiocyanate | 0.015 |

The enzymatic solution was prepared by admixing the starch, sorbitol, water, glycerine and glucose and heating the admixture to 212° F. to form a solution, and thereafter cooling the solution to 130° F. and adding, with stirring, glucose oxidase, myeloperoxidase and potassium thiocyanate to obtain the enzymatic coating composition. The viscosity of the solution was 1,900 centipoises.

EXAMPLE 6

This example illustrates an enzymatic coating solution containing gelatin and carboxymethylcellulose together with hexose, hexose peroxidase and myeloperoxidase.

| Composition | Weight, grams |
| --- | --- |
| Gelatin | 10 |
| Carboxymethylcellulose | 3 |
| Sorbitol | 30 |
| Water | 50 |
| Hexose | 7 |
| Hexose oxidase (100 IU) | 0.001 |
| Myeloperoxidase (200 IU) | 0.002 |

The enzymatic solution was prepared by admixing the gelatin, carboxymethylcellulose, sorbitol, water and hexose and heating the admixture to 212° F. to form a solution and thereafter cooling the solution to 125° F. and adding, with stirring, the enzymes to obtain the enzymatic coating composition. The viscosity of the solution was 9,000 centipoises.

EXAMPLE 7

This example illustrates an enzymatic coating solution containing carboxymethylcellulose together with glucose, glucose oxidase, lactoperoxidase and potassium thiocyanate.

| Composition | Weight, grams |
| --- | --- |
| Carboxymethylcellulose | 12 |
| Glycerine | 50 |
| Water | 35 |
| Glucose | 3 |
| Glucose oxidase (100 IU) | 0.001 |
| Lactoperoxidase (50 IU) | 0.0005 |
| Potassium thiocyanate | 0.150 |
| Flavor | Q.S |
| Color | Q.S |

The enzymatic solution was prepared in accordance with the general procedure described in Example 3. The viscosity of the solution was 2,500 centipoises.

EXAMPLE 8

This example illustrates an enzymatic coating solution containing gelatin, hydrogenated starch, pumice, glucose oxidase, lactoperoxidase and sodium thiocyanate.

| Composition | Weight, grams |
| --- | --- |
| Gelatin | 30 |
| Hydrogenated starch | 15 |
| Water | 35 |
| Pumice | 10 |
| Glucose | 8 |
| Mineral oil | 2 |
| Glucose oxidase (5,000 IU) | 0.050 |
| Lactoperoxidase (800 IU) | 0.008 |
| Sodium thiocyanate | 0.090 |

The enzymatic solution was prepared in accordance with the general procedure described in Example 5. The viscosity of this solution was greater than 4,000 centipoises.

EXAMPLE 9

This example illustrates an enzymatic coating solution containing gelatin, glucose, glucose oxidase, lactoperoxidase, sodium thiocyanate, glucosamine, and N-acetyl glucosamine.

| Composition | Weight, grams |
| --- | --- |
| Gelatin | 30 |
| Glycerine | 30 |
| Water | 30 |
| Glucose | 3 |
| Glucose oxidase (4,000 IU) | 0.040 |
| Lactoperoxidase (1,200 IU) | 0.012 |
| Sodium thiocyanate | 0.050 |
| Glucosamine | 0.012 |
| N-acetyl glucosamine | 0.01 |

The enzymatic solution was prepared in accordance with the general procedure described in Example 5. The viscosity of the solution was greater than 5,000 centipoises.

EXAMPLE 10

This example illustrates a 2-part coating system where the enzyme and its substrate are separately applied to the chewable base in order to prevent the enzymatic system from reacting prematurely. This method is useful where the application method calls for a higher water content or a lower viscosity than that hereinabove specified.

10(a)

| Part A | Part B |
| --- | --- |
| Water | Water |
| Gelatin | Gelatin |
| Glucose | Glucose oxidase |
| Potassium thiocyanate | Lactoperoxidase |

10(b)

| Part A | Part B |
| --- | --- |
| Water | Water |
| Gelatin | Gelatin |
| Glucose | Glucose oxidase |
| Lactoperoxidase | |
| Potassium thiocyanate | |

Parts A and B of examples 10(a) and 10(b) can be prepared in accordance with the general procedure described in Example 2. It is important to apply one part of the 2-part system to the chewable base and allow it to dry before applying the second part thereto.

Adjunct antibacterial agents can be added to the enzymatic formulation of this invention such as the enzyme lysozyme and the protein lactoferrin.

In view of the foregoing descriptions and examples, it will become apparent to those of ordinary skill in the art that equivalent modifications thereof may be made without departing from the spirit and scope of this invention.

That which is claimed is:

1. An orally chewable, enzymatically coated, pet product comprising raw hide, beef hide or non-toxic plastic wherein an enzymatic coating is developed, in substantially dry form, from an enzymatic solution comprising a fluidic component and an enzymatic component:

said fluidic component containing water and non-toxic water soluble thickener in an amount to provide the enzymatic solution with a viscosity from about 1,000 to about 50,000 centipoises; and said enzymatic component comprising an enzymatic system containing, per gram of fluidic component, from about 0.015 to about 0.6 millimole of oxidizable substrate and from about 0.5 to about 5,000 International Units of oxidoreductase enzyme specific to such substrate for producing hydrogen peroxide upon oral chewing of the enzymatically coated pet product.

2. The product of claim 1 wherein the amount of water soluble thickener in the said solution is so selected as to provide the solution with a viscosity of at least about 5,000 centipoises.

3. The product of claim 1 wherein the amount of water soluble thickener in the said solution is so selected as to provide the solution with a viscosity of at least about 10,000 centipoises.

4. The product of claim 1 wherein the water soluble thickener in the said solution comprises hydrophilic colloid.

5. The product of claim 1 wherein the water soluble thickener in the said solution is a member selected from the group consisting of gelatin, carboxymethylcellulose, agar-agar, high viscosity starch, polyvinyl alcohol, carrageen and mixtures thereof.

6. The product of claim 1 wherein the oxidizable substrate is Beta-D-Glucose and the oxidoreductase enzyme is glucose oxidase.

7. The product of claim 1 wherein the oxidizable substrate is hexose and the oxidoreductase enzyme is hexose oxidase.

8. The product of claim 1 wherein the enzymatic component also contains from about 0.1 to about 10,000 International Units of peroxidatic peroxidase and from about 0.0001 to about 0.01 millimole of an alkali metal salt of an oxygen accepting anion selected from the group consisting of thiocyanate, chloride and iodide or a mixture of such salts for interacting with hydrogen peroxide to produce oxidized anionic bacterial inhibitor.

9. The product of claim 8 wherein the peroxidase is lactoperoxidase and the alkali metal salt is alkali metal thiocyanate.

10. The product of claim 1 which further contains an effective amount of an augmenting anti-bacterial agent selected from the group consisting of lysozyme, lactoferrin and mixtures thereof.

11. A method for preparing an orally chewable, enzymatically coated pet product comprising raw hide, beef hide or non-toxic plastic which comprises:

applying an enzymatic solution comprising a fluidic component and an enzymatic component to a chewable product, wherein:

(1) said fluidic component contains water and non-toxic water soluble thickener in an amount to provide the enzymatic solution with a viscosity from about 1,000 to about 50,000 centipoises; and (2) said enzymatic component comprises an enzymatic system containing, per gram of fluidic component, from about 0.015 to about 0.6 millimole of oxidizable substrate and from about 0.5 to about 5,000 International Units of oxidoreductase enzyme specific to such substrate for producing hydrogen peroxide upon oral chewing of the enzymatically coated product; and (b) thereafter drying the coated product.

12. The method of claim 11 wherein the amount of water soluble thickener in the fluidic component is so selected as to provide the solution with a viscosity of at least about 5,000 centipoises.

13. The method of claim 11 wherein the amount of water soluble thickener in the fluidic component is so selected as to provide the solution with a viscosity of at least about 10,000 centipoises.

14. The method of claim 11 wherein the amount of water soluble thickener in the fluidic component is so selected as to provide the solution with a viscosity of at least about 10,000 centipoises.

15. The method of claim 11 wherein the oxidizable substrate is Beta-D-Glucose and the oxidoreductase enzyme is glucose oxidase.

16. The method of claim 11 wherein the enzymatic component also contains from about 0.1 to about 10,000 International Units of peroxidatic peroxidase and from about 0.0001 to about 0.01 millimole of an alkali metal salt of an oxygen accepting anion selected from the group consisting of thiocyanate, chloride and iodide or a mixture of such salts for interacting with hydrogen peroxide to produce oxidized anionic bacterial inhibitor.

17. The method of claim 16 wherein the peroxidase is lactoperoxidase and the alkali metal salt is alkali metal thiocyanate.

18. The method of claim 11 wherein the water soluble thickener is a member selected from the group consisting of gelatin, carboxymethylcellulose, agar-agar high viscosity starch, polyvinyl alcohol, carrageen, and mixtures thereof.

* * * * *